United States Patent [19]
Takahashi et al.

[11] Patent Number: 5,871,439
[45] Date of Patent: *Feb. 16, 1999

[54] ENDOSCOPE SYSTEM TRANSMITTING A MAGNIFICATION RATIO TO AN EXTERNAL PROCESSING DEVICE

[75] Inventors: Tadashi Takahashi; Masaaki Nakashima, both of Tokyo, Japan

[73] Assignee: Asahi Kogaku Kogyo Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 588,261

[22] Filed: Jan. 18, 1996

[30] Foreign Application Priority Data

Jan. 18, 1995 [JP] Japan .................................. 7-005365

[51] Int. Cl.$^6$ .................................................. A61B 1/045
[52] U.S. Cl. ............................................ 600/118; 348/74
[58] Field of Search ................................. 600/117, 118, 600/109; 348/65, 72, 74, 76

[56] References Cited

U.S. PATENT DOCUMENTS

| | | |
|---|---|---|
| 4,343,300 | 8/1982 | Hattori . |
| 4,706,118 | 11/1987 | Kato et al. . |
| 4,816,909 | 3/1989 | Kimura et al. ................... 600/109 X |
| 4,827,908 | 5/1989 | Matsuo ................................ 600/109 |
| 5,031,036 | 7/1991 | Kikuchi et al. ......................... 348/65 |
| 5,305,098 | 4/1994 | Matsunaka et al. .................... 348/65 |
| 5,412,478 | 5/1995 | Ishihara et al. . |

FOREIGN PATENT DOCUMENTS

| | | |
|---|---|---|
| 61-179129 | 8/1986 | Japan . |
| 63-316247 | 12/1988 | Japan . |
| 1185239 | 7/1989 | Japan . |
| 1213615 | 8/1989 | Japan . |
| 1306810 | 12/1989 | Japan . |
| 2140712 | 5/1990 | Japan .................................. 600/118 |
| 2-42489 | 9/1990 | Japan . |
| 3114433 | 5/1991 | Japan . |
| 3-37405 | 6/1991 | Japan . |
| 5-95900 | 4/1993 | Japan . |
| 670883 | 3/1994 | Japan .................................. 600/118 |
| 6169886 | 6/1994 | Japan . |

*Primary Examiner*—John P. Leubecker
*Attorney, Agent, or Firm*—Greenblum & Bernstein, P.L.C.

[57] ABSTRACT

An endoscope system, having an exchangeable endoscope device, for outputting an image data and a video processing device. The endoscope device is provided with a memory for storing data related to an endoscope type. The video processing device reads the data related to the endoscope type, and transmits the data to a peripheral device. The video processing device has a display, and is capable of displaying an image on the display in accordance with a selected one of a plurality of magnification ratios. The selected magnification ratio is also transmitted to the peripheral device.

22 Claims, 5 Drawing Sheets

ENDOSCOPE SYSTEM TRANSMITTING A MAGNIFICATION RATIO TO AN EXTERNAL PROCESSING DEVICE

BACKGROUND OF THE INVENTION

The present invention relates to an endoscope system in which an image of an object is formed on an imaging device of an electronic endoscope and displayed on a monitor.

Conventionally, an electronic endoscope has an imaging device, such as a CCD (Charge Coupled Device), and a display device, such as an LCD monitor. Some recent electronic endoscopes also have an output for transmitting a video signal to a peripheral device, such as an external image processing device, external display device or image recording device.

In general, the image is displayed on a portion of the monitor or external display device. The size of the image depends on the size and resolution (i.e., number of pixels) of the imaging device, which in turn depends on the type of endoscope being used.

If only a portion of an entire image frame is required to be processed, then the processing the entire image data will be inefficient. Conversely, if only a portion of the image data is processed, but all of the image data should be processed, it will not be possible to view the entire image.

A similar problem arises when the image data is recorded. If all the image data is recorded even though only a portion of the image data is required, then more memory or data storage capacity of the recording medium is used than would otherwise be necessary. Conversely, if image data corresponding to a portion of the image is recorded, but all of the image data should be recorded, then an incomplete image will be recorded.

SUMMARY OF THE INVENTION

It is therefore an object of the invention to provide an endoscope system which is capable of supplying data for an appropriate area of an image frame to at least one peripheral device.

For the above object, according to an aspect of the present invention, there is provided an endoscope system which includes an endoscope device for outputting image data, the endoscope device having a memory for storing data related to a type of the endoscope; a video processing device for processing the image data, the endoscope device being detachably connected to the video processing device, the video processing device being capable of reading the data related to the type of endoscope; and at least one peripheral device that is detachably connected to the video processing device. The video processing device is capable of transmitting ,an output data corresponding to the data related to the type of the endoscope to peripheral device.

Optionally, the output data may include the type of the endoscope.

The endoscope may be provided with a display for displaying an image processed by the video processing device. The displayed image can be magnified in accordance with one of a plurality of magnification ratios. Further, the video processing device can transmit the magnification ratio to the peripheral device.

The video processing device is capable of transmitting the image data as well as the data related to the type of the endoscope device, to the peripheral device.

Accordingly, the peripheral device can process the image data in accordance with the data related to the type of endoscope. Further, the peripheral device can determine the portion of the image data to be processed in accordance with data related to the type of the endoscope and the magnification ratio.

The endoscope device can be an electronic endoscope provided with an imaging device, such as CCD (charge coupled device; which receives an optical image and outputs an image signal corresponding to the received image.

Optionally, the data related to the type of endoscope device may include data representing the number of pixels of the charge coupled device.

Alternatively, the endoscope device may include an optical endoscope provided with an eyepiece lens, an object being observed through the eyepiece lens; and an imaging device which is coupled to the eyepiece lens. In this case, the imaging device receives an optical image through the eyepiece lens and converts the optical image into image data.

Optionally, the optical endoscope may have a memory for storing data related to a characteristic of the endoscope. Further, the imaging device may have another memory for storing data related to a characteristic of the imaging device.

According to another aspect of the invention, there is provided an endoscope system which includes an exchangeable endoscope device for outputting image data; a video processing device for processing the image data; a device for displaying an image in accordance with the image data processed by the video processing device; being; and a device for identifying a currently coupled endoscope device; at least one peripheral device detachably connected to the video processing device; a device for transmitting the electronic image data output by the endoscope device; and a device for transmitting data related to the currently coupled endoscope device to the at least one peripheral device.

Optionally, the video processing device is capable of processing the image data so that the display device displays the image at more than one magnification ratio. Further, the device for transmitting data related to the currently coupled endoscope device is capable of transmitting a magnification ratio currently available on the display device.

DESCRIPTION OF THE PREFERRED EMBODIMENTS

Figure 1:
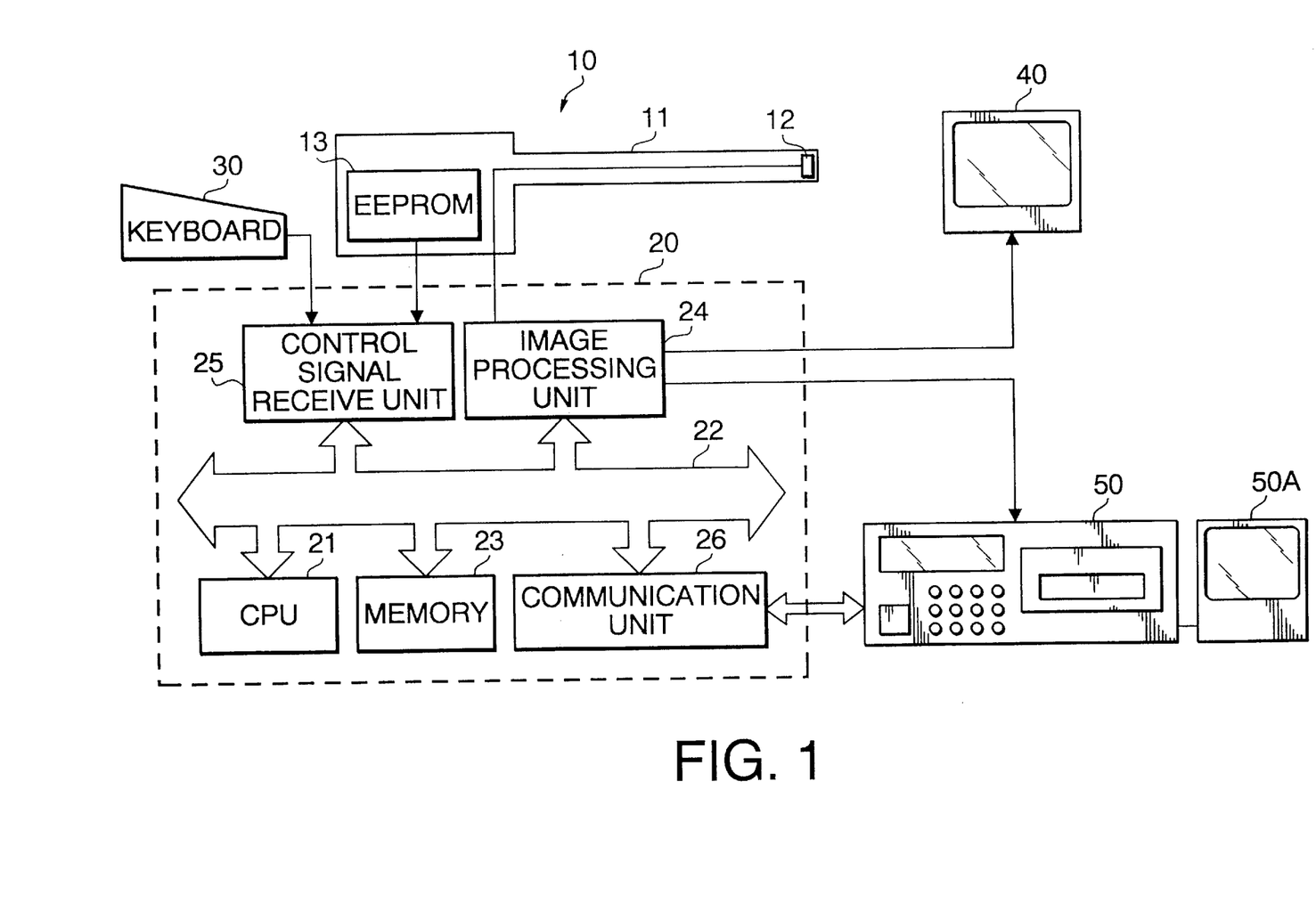
FIG. 1 shows a block diagram of an endoscope system embodying the present invention.

FIG. 1 shows a block diagram of a first embodiment of an endoscope system.

The endoscope system includes an electronic endoscope 10 (hereinafter referred to as endoscope 10) or means for outputting image data, a video processor 20, a keyboard 30, means for indicating, such as a display 40, and an image data processing device 50. The endoscope 10 is detachably coupled to the video processor 20. In the preferred embodiment, the keyboard 30 is integrally provided with the video processor 20.

An image of an object to be observed is formed by an optical system (not shown) and is detected by an imaging device 12, such as a CCD. The imaging device 12 is provided at a tip of an insertion portion 11 of the endoscope 10. The endoscope 10 has an EEPROM 13 which stores the endoscope type and information related to a number of pixels of the imaging device 12. The endoscope types include endoscopes for insertion into the digestive tract of a human body and endoscopes for insertion into the respiratory system of a human body.

The video processor 20 has a CPU 21 and a system bus 22. A memory 23, an image processing unit 24, a control signal input unit 25, and a communication unit 26 are also connected to the system bus 22.

The memory 23 has a RAM which is used for temporarily storing various data to be used for calculation as well as the calculation results. The data stored in the memory 23 is transmitted to the image data processing device 50 through the communication unit 26. The memory 23 also has a ROM for storing various constants, a look-up table (described later), and various programs to be executed by the CPU 21.

The image processing unit 24 receives the image signal transmitted from the imaging device 12, performs various processing, such as a gamma correction, and outputs an NTSC format video signal to the display 40. The image processing unit 24 also outputs an RGB signal to the image data processing device 50. The image processing device 50 that is connected to the video processor 20 is a well known device.

Control signals are transmitted from the keyboard 30 to the control signal input unit 25. The keyboard 30 includes a magnify key which controls a magnification ratio of an image shown on the display 40. Data stored in the EEPROM 13 of the endoscope 10 is also transmitted to the control signal input unit 25. The communication unit 26 transmits and receives signals from the is image data processing device 50.

Figure 2:
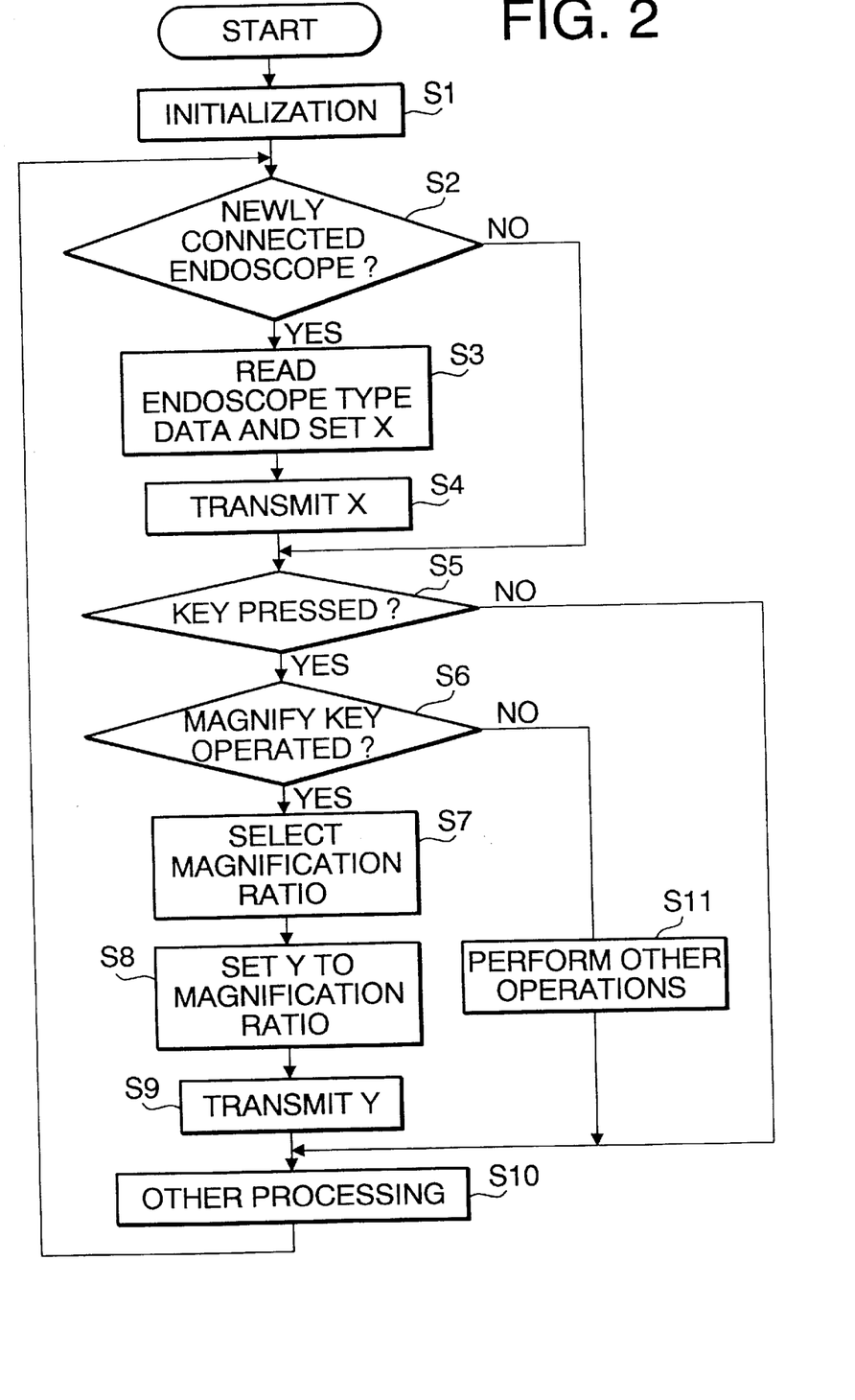
FIG. 2 is a flowchart showing a main procedure of the endoscope system shown in FIG. 1, according to a first embodiment of the present invention.

FIG. 2 is a flowchart illustrating a main procedure of the endoscope system according to a first embodiment of the present invention. The main procedure is stored in the memory 23 as a program and executed by the CPU 21.

In step S1, an initialization procedure is executed. In the initialization procedure, the variables to be used for calculation are set with default values.

In step S2, the CPU 21 detects whether the endoscope 10 has just been connected to the video processor 20. In this embodiment, one of the data lines between the video processor 20 and the endoscope 10 is monitored. If the data line has changed from being open (i.e., floating) to closed (i.e. tied LOW) within a predetermined time period, then the video processor 20 determines that the endoscope 10 has just been connected. If the endoscope 10 was already connected to the video processor 20 (S2:N), steps S3 and S4 (described below) are skipped.

If the endoscope 10 was just connected (S2:Y), the CPU 21 reads the data related to the endoscope type from the EEPROM 13 of the endoscope in step S3. Also in step S3, a variable X is set with a value which indicates the type of the endoscope, and is stored temporarily in the memory 23. In the preferred embodiment, the value of the variable X represents the number of pixels of the imaging device 12. The value of the variable X is then transmitted from the memory 23 through the communication unit 26 to the image data processing device 50, in step S4.

In step S5, the CPU 21 determines whether the keyboard 30 is operated. If no keys are operated (S5:N), steps S6 through S9 as well as step S11 (described below) ate skipped. If a key has been operated (S5:Y), then step S6 determines whether the operated key is a magnify key for magnifying the observed image which is displayed on the display 40. If the operated switch is not the magnify key (S6:N), other operations corresponding to the depressed key is executed in step S11. In the preferred embodiment, other operations include the adjustment of the contrast, the color balance, and the brightness of the image.

If the magnify key was depressed in step S6, then step S7 selects the magnification ratio. In the video processor 20, the magnification ratio is cycled among the ratios 1.0, 1.5 and 2.0 upon every depression of the magnify key. Further, in step S7, an image magnifying processing is executed by the image processing unit 24 so that the image is displayed on the monitor 40 with the designated magnification. Step S8 sets a variable Y with the selected magnification ratio (i.e., 1.0, 1.5 or 2.0), and stores the variable Y, temporarily in the memory 23. The variable Y is then transmitted from the memory 23 through the communication unit 26 to the image data processing device 50, in step S9. Then, in step S10, other processing such as displaying the date or time, is executed. Control then returns to step S2.

The magnification ratio described above is the ratio of the size of the displayed image with respect to a standard image size displayed on the monitor 40. In the preferred embodiment, as mentioned above, the magnification ratio can be 1:1 (i.e., the standard image size with no magnification), 1:1.5 or 1:2.

Figure 4:
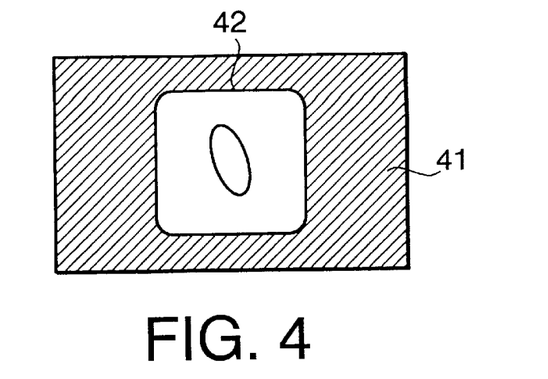
FIG. 4 shows an example image, viewed using the electronic endoscope shown in FIG. 1.
Figure 5:
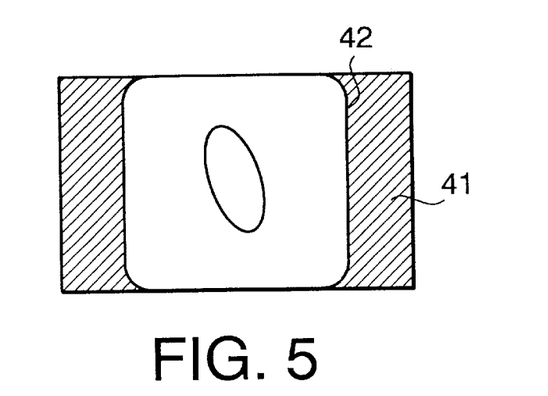
FIG. 5 shows the image of FIG. 4 magnified 1.5 times, as viewed through the electronic endoscope shown in FIG. 1.
Figure 6:
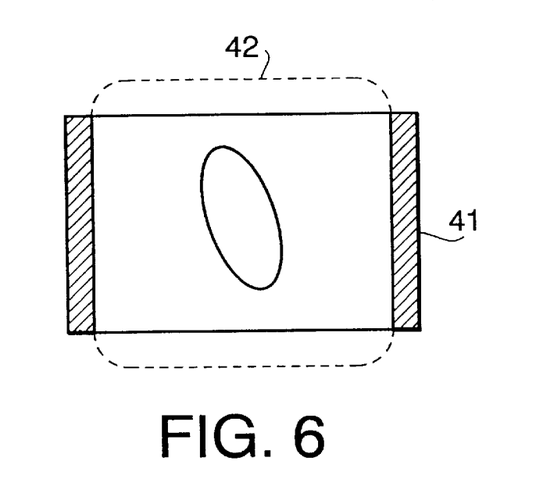
FIG. 6 shows the image of FIG. 4 magnified 2 times, as viewed through the electronic endoscope shown in FIG. 1.

These three image sizes are shown in FIGS. 4, 5 and 6, respectively. Each of these figures shows an image 42 of the object displayed on a screen 41 of the monitor 40.

The image data processing device 50 calculates the size of the image after the magnification of the image has been selected based on the variable Y transmitted from the memory 23 through the communication unit 26, and determines the area of the imaging device 12 to which the image processing operation is to be applied.

The image data processing device 50 executes an image processing operation in accordance with the variables X and Y received from the memory 23 through communication unit 26.

The image processing device 50 also has a memory for storing the variables X and Y.

More specifically, the image data processing device 50 determines the portion of the image data to be processed based on the variables X and Y. The processing operation includes an edge detection process, a noise reduction process, and an image sharpening operation, etc. The processed image is displayed on a monitor 50A which is connected to the image processing device.

It should be noted that the area of the image displayed on the monitor 40 corresponds to the image displayed on the monitor 50A. If the magnification ratio selected in the video processing unit 20 is 2.0, a portion of the image detected by the CCD 12 is displayed on the monitor 40. In this case, the data processing device 50 processes only a portion of the image data, based on the variables X and Y, which corresponds to the area displayed on the monitor 40. This prevents unnecessary image processing and therefore improves the efficiency of the data processing operation.

The image data processing device 50 determines the length "a" of one side of an image area displayed on the monitor 50A when the magnification ratio is 1.0, from the value of the stored variable X, by referring to an internally stored look-up table. The length of the side of the image displayed on the monitor 50A is calculated by multiplying "a" with the variable Y. The area of the image to which the processing is applied can be determined based on the length of the side of the image as calculated above.

Figure 3:
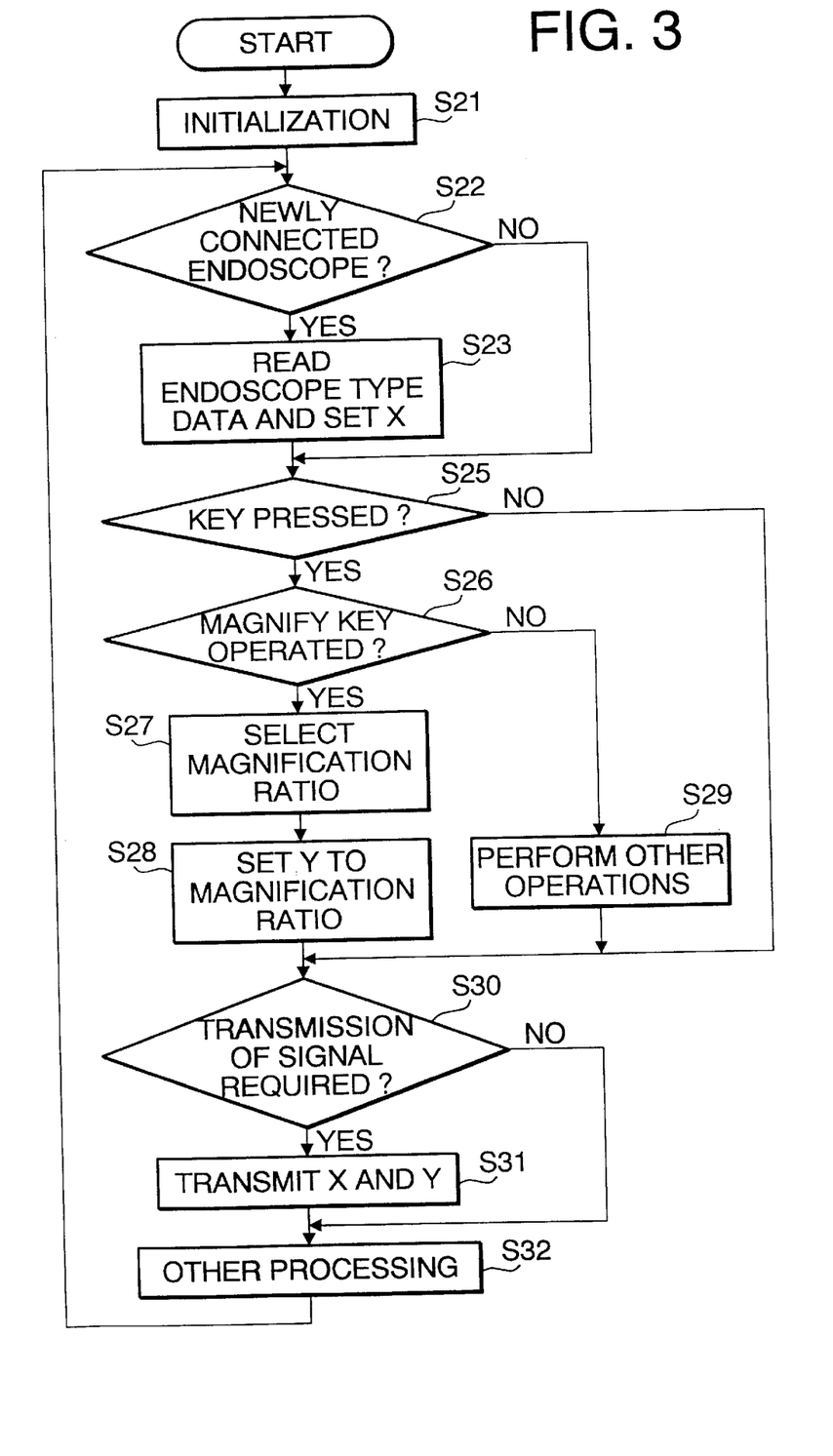
FIG. 3 is a flowchart illustrating a main procedure of the endoscope system shown in FIG. 1, according to a second embodiment of the present invention.

FIG. 3 is a flowchart illustrating a main procedure of the endoscope system according to a second embodiment of the present invention. The physical construction of the endoscope system is similar to that of the first embodiment. Further, in the second embodiment, the main procedure is also stored as a program in the memory 23 and is executed by the CPU 21.

In step S21, an initialization procedure is executed.

In step S22, the CPU 21 detects whether the endoscope 10 has just been connected to the video processor 20. If the endoscope 10 was already connected to the video processor 20 (S22:N), then step S23 is skipped. If the endoscope 10 was just connected (S22:Y), the CPU 21 reads the data related to the endoscope type from the EEPROM 13 of the endoscope in step S23. Also in step S23, the variable X is set with a value which indicates the type of the connected endoscope 10, and is temporarily stored in the memory 23.

In step S25, the CPU 21 determines whether the keyboard 30 is operated. If no keys are operated (S25:N), steps S26 through S29 (described below) are skipped. If a key has been operated (S25:Y), then step S26 determines whether the operated key is the magnify key. If the operated key is not the magnify key (S26:N), then an operation corresponding to the depressed key is executed in step S29.

If the magnify key was depressed in step S26, then step S27 selects the magnification ratio. As described above for the first embodiment, the magnification ratio is cycled among the ratios 1.0, 1.5 and 2.0, upon every depression of the magnify key. Further, in step S27, the image magnifying processing is executed by the image processing unit 24 so that the image is displayed on the monitor 40 with the designated magnification. Step S28 sets a variable Y with the selected magnification ratio (i.e., 1.0, 1.5 or 2.0). The variable Y is temporarily stored in the memory 23.

In step S30, the CPU 21 determines whether a transmit data signal has been transmitted to the video processing unit 20 from the image data processing device 50. The data transmit signal instructs the transmission of data from the memory 23 through the communication unit 26 to the image data processing device 50. If the transmit data signal is not input (S30:N), the control proceeds to step S32 where other processing, such as displaying the date or time, is executed control then returns to step S22.

If the signal is input (S30:Y), the variables X and Y which have been set are transmitted from the memory 23 through the communication unit 26 to the image data processing device 50, in step S31. Control then proceeds to step S32, where other processing is executed.

The image data processing device 50 determines the area of the image to be processed based on the variables X and Y, and performs processing. The processed image is displayed on the monitor 50A connected to the image data processing device 50.

The invention can be modified; such as the number of pixels of the imaging device 12 being stored in the EEPROM 13 of the endoscope 10 instead .oif the type of the imaging device 12, and accordingly the number of the pixels is transmitted to the image data processing device 50 from the communication unit 26.

Further, the invention is not limited to the electronic endoscope employing the built-in imaging device, but can be applied to a device constructed such that the imaging device is attached to the eyepiece of an optical endoscope utilizing an image guide fiber.

Figure 7:
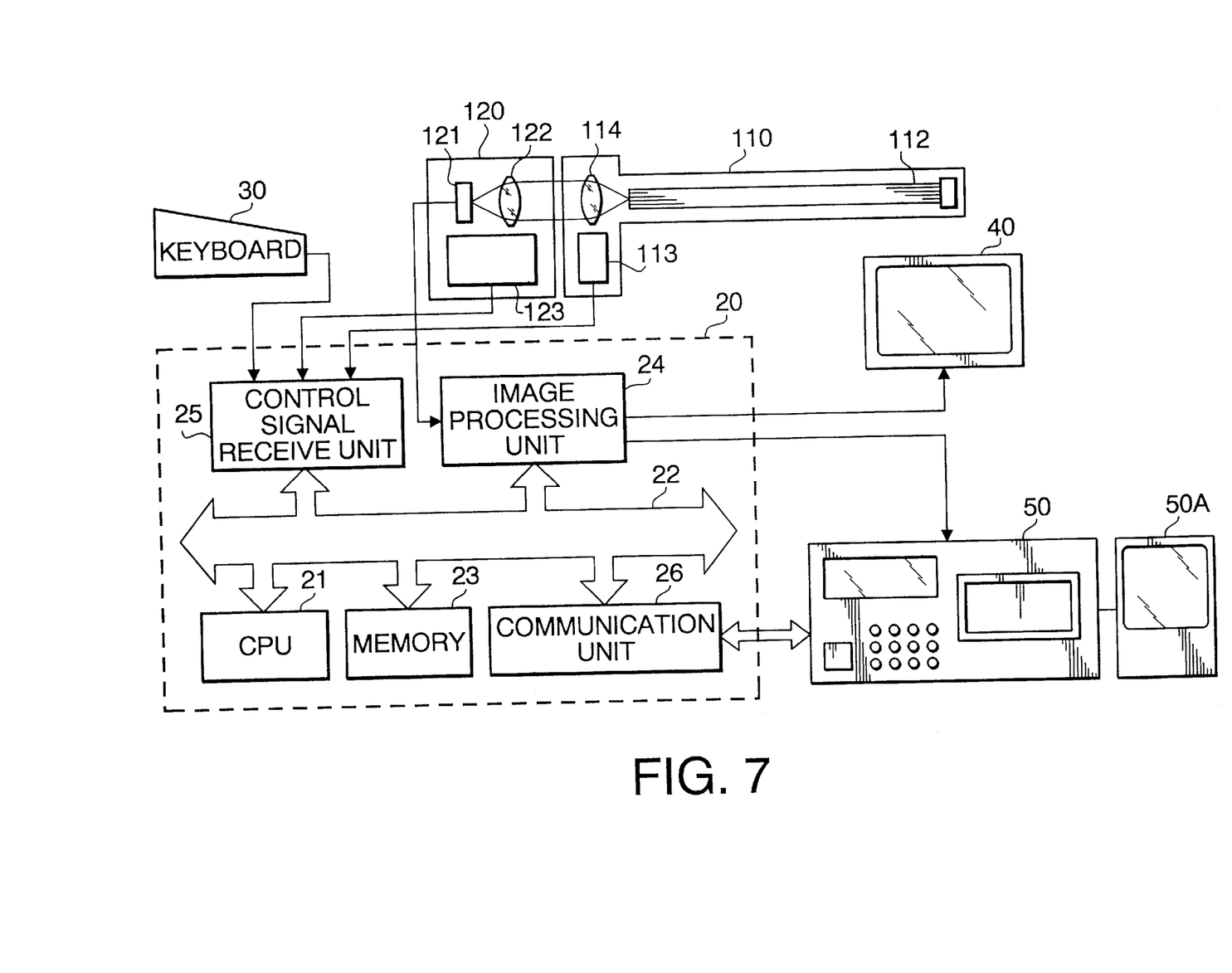
FIG. 7 shows a block diagram of an endoscope system according to a third embodiment of the present invention.

FIG. 7 shows a block diagram of an endoscope system according to a third embodiment of the present invention. The endoscope system employs an optical endoscope 110 and an imaging device, such as a TV camera having a lens and a CCD 121.

The endoscope system shown in FIG. 7 includes an endoscope 110 having an image fiber 112, an eyepiece lens 114, and a memory 113. A photographing lens 122 of the TV camera 120 is coupled to the eyepiece lens 114. The TV camera 120 is further provided with a CCD 121 and a memory 123. The endoscope system also includes the video processor 20, the keyboard 30, the display 40, and the image data processing device 50 which are similar to those provided in the first and second embodiments of the endoscope system shown in FIG. 1.

In the endoscope system shown in FIG. 71, the image of the object is transmitted through the image fiber 112. The image is formed on the CCD 121 through the eyepiece lens 114 and the photographing lens 122. The image signal is then transmitted from the CCD 121 to the image processing unit 24.

The memory 113 of the optical endoscope 110 is an EEPROM, in which a diameter D of the image fiber 112, and a focal length Foc of the eyepiece lens 114 are stored. The memory 123 of the TV camera 120 is also an EEPROM, where a length L of an effective shorter side of the CCD 121, and a focal length Ft of the photographing lens 122 are stored. From these values, a ratio R of the length of the side of an image displayed on the monitor 50A with respect to the side of the monitor 50A (which corresponds to the value "a" in the first and second embodiment) can be obtained in accordance with the following equation.

$$R=(D*Ft/Foc)/L=(Ft/L)*(D/Foc) \qquad (1)$$

In view of the above, the memory 123 of the TV camera may store the values Ft and L, or a value Ft/L. Similarly, the memory 113 of the endoscope 110 may store two values D and Foc, or a single value of D/Foc.

The CPU 21 calculates the ratio R and sets the variable X to have the value of the ratio R. Further, in the third embodiment, the magnification ratio is calculated in a similar manner as described above for the first or the second embodiment. The variable Y is then set with the magnification ratio.

According to the invention, data related to the type of endoscope or the type of imaging device, and magnification ratio are output, the peripheral devices are capable of determining the area of an image to be processed. Therefore, only an appropriate area of an image can be processed, which makes the processing executed efficiently.

The present disclosure relates to a subject matter contained in Japanese Patent Application No. HEI 7-005365, filed on Jan. 18, 1995, which is expressly incorporated herein by reference in its entirety.

What is claimed is:

1. An endoscope system, comprising:

means for outputting image data, said outputting means having a memory that stores data related to a type of said outputting means;

means for processing said image data, said outputting means being detachably connected to said processing means, said processing means reading said data related to said type of said outputting means;

means for indicating said image data processed by said processing means; and at least one peripheral device that further processes said image data, said at least one peripheral device being detachably connected to said processing means, wherein said processing means processes said image data such that said image data is indicated by said indicating means in accordance with one of a plurality of magnification ratios, said processing means transmitting output data corresponding to said data related to said type of outputting means and data corresponding to said one of said plurality of magnification ratios to said peripheral device.

2. An endoscope system, comprising:

an exchangeable endoscope device for outputting image data;

video processing means for processing said image data, said exchangeable endoscope device being coupled to said video processing means;

means for displaying an image in accordance with said image data processed by said video processing means;

means for identifying a currently coupled endoscope device;

at least one peripheral device that further processes said image data, said at least one peripheral device being detachably connected to said video processing means;

means for transmitting said image data output by said video processing means; and means for transmitting data related to said currently coupled endoscope device to said at least one peripheral device, said video processing means processing said image data so that said displaying means displays said image at more than one magnification ratio, said data transmitting means transmitting a magnification ratio in accordance with a magnification ratio of said image being displayed by said displaying means.

3. The endoscope system of claim 2, wherein said endoscope device comprises an electronic endoscope having an imaging device that receives an optical image and outputs an image signal corresponding to said received optical image.

4. The endoscope of claim 3, wherein said imaging device comprises a charge coupled device.

5. The endoscope of claim 2, wherein said endoscope device comprises:

an optical endoscope; and an imaging device coupled to said optical endoscope to receive an optical image from said optical endoscope for conversion to electronic image data.

6. The endoscope of claim 2, wherein said at least one peripheral device improves a signal quality of said image data.

7. An endoscope system, comprising:

an endoscope device that outputs image data, said endoscope device having a memory that stores data related to a type of said endoscope device;

a video processing device that processes said image data, said endoscope device being detachably connected to said video processing device, said video processing device reading said data related to said type of said endoscope device;

a display that displays said image data processed by said video processing device; and at least one peripheral device that further processes said image data, said at least one peripheral device being detachably connected to said video processing device, wherein said video processing device processes said image data such that said image data is displayed on said display in accordance with one of a plurality of magnification ratios, said video processing device transmitting output data corresponding to said data related to said type of endoscope device and data corresponding to said one of said plurality of magnification ratios to said peripheral device.

8. The endoscope system according to claim 1, wherein said output data represents said type of said endoscope device.

9. The endoscope system according to claim 1, wherein said video processing device has an operation member for selecting said one of said plurality of magnification ratios.

10. The endoscope system according to claim 1, wherein said video processing device is capable of transmitting said image data to said peripheral device.

11. The endoscope system according to claim 1, wherein said endoscope device comprises an electronic endoscope provided with an imaging device for receiving an optical image and outputting an image signal corresponding to said received image.

12. The endoscope system according to claim 11, wherein said output data includes data related to a type of said imaging device.

13. The endoscope system according to claim 12, wherein said imaging device comprises a charge coupled device.

14. The endoscope system according to claim 13, wherein said output data includes data representing a number of pixels of said charge coupled device.

15. The endoscope system according to claim 13, wherein said endoscope device comprises:

an optical endoscope provided with an eyepiece lens, an object being able to be observed through said eyepiece lens; and an imaging device to be coupled to said eyepiece lens, said imaging device receiving an optical image through said eyepiece lens and converting said optical image into electronic image data.

16. The endoscope system according to claim 15, wherein said optical endoscope has said memory for storing data related a characteristic of said optical endoscope.

17. The endoscope system according to claim 16, wherein said optical endoscope includes an image fiber for transmitting an optical image, and wherein said data related to a characteristic of said optical endoscope represents a diameter of said image fiber, and a focal length of said eyepiece lens.

18. The endoscope system according to claim 17, wherein said imaging device comprises a charge coupled device for receiving an optical image and outputting an image signal corresponding to said received image, a lens for receiving light from said eyepiece lens of said optical endoscope and forming an optical image on said charge coupled device, and a memory for storing data related to a characteristic of said charge coupled device and said lens for receiving light from said eyepiece lens of said optical endoscope.

19. The endoscope system according to claim 15, wherein said imaging device comprises an imaging element for receiving an optical image and converting a received optical image into said electronic image data, and a lens for forming an image on said imaging element.

20. The endoscope system according to claim 1, wherein said peripheral device performs an edge detection on said image data.

21. The endoscope system according to claim 1, wherein said peripheral device reduces noise included in said image data output by said endoscope device.

22. The endoscope system according to claim 1, wherein said peripheral device increases a sharpness of said image data.

* * * * *